(12) United States Patent
McDonell

(10) Patent No.: US 10,369,046 B2
(45) Date of Patent: Aug. 6, 2019

(54) MINIMAL PULSATION OPHTHALMIC PROBE

(71) Applicant: Novartis AG, Basel (CH)

(72) Inventor: Brian W. McDonell, Lake Forest, CA (US)

(73) Assignee: Novartis AG, Basel (CH)

( * ) Notice: Subject to any disclaimer, the term of this patent is extended or adjusted under 35 U.S.C. 154(b) by 206 days.

(21) Appl. No.: 15/284,055

(22) Filed: Oct. 3, 2016

(65) Prior Publication Data

US 2017/0020728 A1 Jan. 26, 2017

Related U.S. Application Data

(63) Continuation of application No. 14/244,986, filed on Apr. 4, 2014, now Pat. No. 9,498,378.

(51) Int. Cl.
*A61F 9/007* (2006.01)

(52) U.S. Cl.
CPC .......... *A61F 9/00736* (2013.01); *A61F 9/007* (2013.01); *A61F 9/00763* (2013.01)

(58) Field of Classification Search
CPC ... A61F 9/00736; A61F 9/007; A61F 9/00763
See application file for complete search history.

(56) References Cited

U.S. PATENT DOCUMENTS

| | | |
|---|---|---|
| 3,884,238 A | 5/1975 | O'Malley et al. |
| 3,994,297 A | 11/1976 | Kopf |
| 4,493,698 A | 1/1985 | Wang et al. |
| 4,530,356 A | 7/1985 | Helfgott et al. |
| 4,577,629 A | 3/1986 | Martinez |
| 4,674,502 A | 6/1987 | Imonti |
| 4,696,298 A | 9/1987 | Higgins et al. |
| 4,757,814 A | 7/1988 | Wang et al. |
| 4,819,635 A | 4/1989 | Shapiro |
| 4,841,984 A | 6/1989 | Armeniades et al. |
| 4,909,249 A | 3/1990 | Akkas et al. |
| 4,940,468 A | 7/1990 | Petillo |
| 4,986,827 A | 1/1991 | Akkas et al. |
| 5,019,035 A | 5/1991 | Missirlian et al. |
| 5,020,535 A | 6/1991 | Parker et al. |
| 5,024,652 A | 6/1991 | Dumenek et al. |
| 5,047,008 A | 9/1991 | De Juan, Jr. et al. |
| 5,059,204 A | 10/1991 | Lawson et al. |
| 5,061,238 A | 10/1991 | Shuler |
| 5,084,052 A | 1/1992 | Jacobs |

(Continued)

FOREIGN PATENT DOCUMENTS

EP 0442851 8/1991

OTHER PUBLICATIONS

Alcon Research, Ltd., Prior Art Statement, U.S. Appl. No. 12/304,792, filed Dec. 11, 2014 (2 pages).

(Continued)

*Primary Examiner* — Julian W Woo

(57) ABSTRACT

An ophthalmic apparatus for performing an ocular surgery may include an ophthalmic probe body having an inner cutting member at least partially disposed within and moveable relative to an aspiration tube within the probe body to facilitate flow of aspiration fluid. A motor within the body may be configured to actuate the inner cutting member relative to the aspiration tube.

14 Claims, 5 Drawing Sheets

(56) References Cited

U.S. PATENT DOCUMENTS

| | | |
|---|---|---|
| 5,176,628 A | 1/1993 | Charles et al. |
| 5,284,472 A | 2/1994 | Sussman et al. |
| 5,354,268 A | 10/1994 | Peterson et al. |
| 5,380,280 A | 1/1995 | Peterson |
| 5,423,844 A | 6/1995 | Miller |
| 5,456,689 A | 10/1995 | Kresch et al. |
| 5,474,532 A | 12/1995 | Steppe |
| 5,520,652 A | 5/1996 | Peterson |
| 5,630,827 A | 5/1997 | Vijfvinkel |
| 5,674,194 A | 10/1997 | Jung et al. |
| 5,733,297 A | 3/1998 | Wang |
| 5,782,849 A | 7/1998 | Miller |
| 5,810,809 A | 9/1998 | Rydell |
| 5,833,643 A | 11/1998 | Ross et al. |
| 5,976,121 A | 11/1999 | Matern et al. |
| 6,010,496 A | 1/2000 | Appelbaum et al. |
| 6,214,017 B1 | 4/2001 | Stoddard et al. |
| 6,485,499 B1 | 11/2002 | Oberkamp et al. |
| 6,488,695 B1 | 12/2002 | Hickingbotham |
| 6,514,268 B2 | 2/2003 | Finlay et al. |
| 6,575,990 B1 | 6/2003 | Wang et al. |
| 6,758,824 B1 | 7/2004 | Miller et al. |
| 6,773,445 B2 | 8/2004 | Finlay et al. |
| 7,458,940 B2 | 12/2008 | Miller |
| 7,549,972 B2 | 6/2009 | Luloh et al. |
| 8,038,692 B2 * | 10/2011 | Valencia ............. A61F 9/00763 606/166 |
| 8,216,246 B2 | 7/2012 | Luloh et al. |
| 8,808,318 B2 | 8/2014 | Auld et al. |
| 9,101,442 B2 | 8/2015 | McDonell |
| 9,381,114 B2 * | 7/2016 | Underwood ..... A61B 17/32002 |
| 9,498,378 B2 * | 11/2016 | McDonell ............... A61F 9/007 |
| 2002/0161398 A1 | 10/2002 | Hickingbotham |
| 2003/0078609 A1 | 4/2003 | Finlay et al. |
| 2005/0080441 A1 | 4/2005 | Dodge et al. |
| 2005/0113715 A1 | 5/2005 | Schwindt et al. |
| 2005/0156387 A1 | 7/2005 | Chen et al. |
| 2006/0271082 A1 | 11/2006 | Kirchhevel et al. |
| 2007/0129732 A1 | 6/2007 | Zacharias |
| 2007/0185514 A1 | 8/2007 | Kirchhevel |
| 2008/0172077 A1 | 7/2008 | Vilencia et al. |
| 2008/0188881 A1 | 8/2008 | Chon |
| 2008/0208233 A1 | 8/2008 | Barnes et al. |
| 2009/0163897 A1 | 6/2009 | Skinner |
| 2009/0234274 A1 | 9/2009 | Luloh et al. |
| 2012/0158006 A1 | 6/2012 | McDonell |
| 2012/0283741 A1 | 11/2012 | Luloh et al. |
| 2013/0053759 A1 | 2/2013 | McCawley |
| 2014/0171995 A1 | 6/2014 | McDonell |
| 2014/0364885 A1 | 12/2014 | Wells et al. |

OTHER PUBLICATIONS

McDonell, "Reduced Friction Vitrectomy Probe" U.S. Appl. No. 61/423,151, filed Dec. 15, 2010, 22 pages.

McDonell, "Vitrectomy Probe with Integral Valve" U.S. Appl. No. 14/090,235, filed Nov. 26, 2013, 27 pages.

International Search Report and Written Opinion issued for PCT/US2015/015254, dated May 15, 2015, 11 pgs.

\* cited by examiner

MINIMAL PULSATION OPHTHALMIC PROBE

CROSS-REFERENCE TO RELATED APPLICATION

The present disclosure is a continuation of U.S. patent application Ser. No. 14/244,986 (now U.S. Pat. No. 9,498, 378), entitled "Minimal Pulsation Ophthalmic Probe," filed Apr. 4, 2014, the entire disclosure of which is hereby incorporated by reference.

FIELD OF THE INVENTION

The present disclosure pertains to ophthalmic probes, systems, and methods. More particularly, but not by way of limitation, the present invention pertains to ophthalmic probes, systems, and methods utilizing an aspiration arrangement that may reduce the impact of fluid pulsations.

BACKGROUND

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member (the needle), a hollow inner cutting member (the cutter) arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

The inner cutting member (or cutter) in conventional vitrectomy cutting probe systems typically connects with a larger tube within the probe via a coupling device. With each cutting cycle, the inner cutting member (or cutter), the coupling device, and the larger tube all axially displace by an amount equal to the cutting stroke length, thereby cutting the vitreous that entered the port. However, the cutting motion also results in a change of the internal fluid volume of the ophthalmic probe. This is due to the difference in internal cross-sectional area between the cutter and the larger tube in conjunction with the axial motion of this transition. The volume change may cause pressure pulses and fluid agitation which could result in fluid pumping, and due to the vacuum present, could drive some gas out of solution, thereby producing bubbles. Further, while most of the excess volume may propagate up the aspiration tube, some of the volume may manifest itself as pulses or even a reversal of flow during vitrectomy cutting. It may also create some agitation that results in gas coming out of solution.

The present disclosure is directed to addressing one or more of the deficiencies in the prior art.

SUMMARY

In some exemplary aspects, the present disclosure is directed to an ophthalmic apparatus for performing an ocular surgery. The apparatus may include an ophthalmic probe body graspable by a user and a cutter extending from the body and comprising an inner cutting member and a needle. The inner cutting member may be at least partially disposed within and moveable relative to the needle, and the inner cutting member may have a lumen having a first diameter. The needle may have a distal end with a port formed therein for receiving patient tissue. An aspiration tube within the probe body may be disposed to extend from the end of the inner cutting member to an aspiration line from the probe body, the aspiration tube having a second diameter greater than the first diameter to facilitate flow of aspiration fluid. A motor within the body may be configured to actuate the inner cutting member relative to the needle and relative to the aspiration tube.

In an aspect, the inner cutting member is coaxial with the aspiration tube. In an aspect, the aspiration tube is fixed in place so as to be stationary relative to the probe body. In an aspect, the ophthalmic apparatus includes a drive shaft connected to the motor and a coupler coupling the drive shaft to the inner cutting member so that when the motor actuates the drive shaft, the coupler actuates the inner cutting member. In an aspect, the drive shaft is larger than the aspiration tube, the aspiration tube being disposed within the drive shaft. In an aspect, the drive shaft is coaxial with the aspiration tube. In an aspect, the aspiration tube extends through a central portion of the motor. In an aspect, the ophthalmic apparatus includes a cutter seal assembly affixed to the aspiration tube, the cutter seal assembly comprising a seal that prevents the passage of fluid. In an aspect, the motor is affixed directly to the inner cutting member.

In some exemplary aspects, the present disclosure is directed to an ophthalmic apparatus for performing an ocular surgery and includes an ophthalmic probe body graspable by a user and a cutter extending from the body and comprising an inner cutting member and a needle. The inner cutting member may be at least partially disposed within and moveable relative to the needle. The inner cutting member may have a lumen having a first diameter, the needle having a distal end with a port formed therein for receiving patient tissue. An aspiration tube may be fixed in place relative to the probe body and may extend from the end of the inner cutting member to an aspiration line from the probe body. The aspiration tube may have a second diameter greater than the first diameter to facilitate flow of aspiration fluid. A motor may be disposed within the body and may be coupled to the inner cutting member. The motor may be configured to actuate the inner cutting member relative to the needle.

In an aspect, the inner cutting member is coaxial with the aspiration tube. In an aspect, the motor is configured to actuate the inner cutting member relative to the aspiration tube. In an aspect, the ophthalmic apparatus includes a drive shaft connected to the motor and a coupler coupling the drive shaft to the inner cutting member so that when the motor actuates the drive shaft, the coupler actuates the inner cutting member. In an aspect, the drive shaft is larger than the aspiration tube, the aspiration tube being disposed within the drive shaft. In an aspect, the drive shaft is coaxial with the aspiration tube. In an aspect, the aspiration tube extends through a central portion of the motor. In an aspect, the ophthalmic apparatus includes a cutter seal assembly affixed to the aspiration tube, the cutter seal assembly comprising a seal that prevents the passage of fluid. In an aspect, the aspiration tube comprises a portion of an aspiration pathway in the probe body, and only the inner cutting member displaces within the aspiration in a manner impacting the volume of the aspiration pathway. In an aspect, the motor is affixed directly to the inner cutting member.

In some exemplary aspects, the present disclosure is directed to methods of driving an inner cutting member of an ophthalmic probe. The methods may include opening an aspiration port in a needle of a distally protruding cutter by driving a motor to drive an inner cutting member in a proximal direction. The aspiration port, the inner cutting member, and an aspiration tube may form a portion of an aspiration pathway through the ophthalmic probe. The inner cutting member may have a first diameter and the aspiration tube may have a second diameter greater than the first diameter. Driving the inner cutting member in the proximal direction may include moving the inner cutting member relative to the aspiration tube. The method may also include closing the aspiration port to cut tissue in the aspiration port by driving the motor in the ophthalmic probe to drive the inner cutting member in the distal direction relative to the needle and displacing the inner cutting member relative to the aspiration tube.

In an aspect, the aspiration tube is fixed in place within the ophthalmic probe and the volume of the aspiration pathway in the ophthalmic probe changes only by the volume equal to the axial displacement of the inner cutting member. In an aspect, driving a motor to drive an inner cutting member includes driving a drive shaft connected to the motor, and driving a coupler connected to the drive shaft, the coupler being connected to the inner cutting member at a location distal of the aspiration tube.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
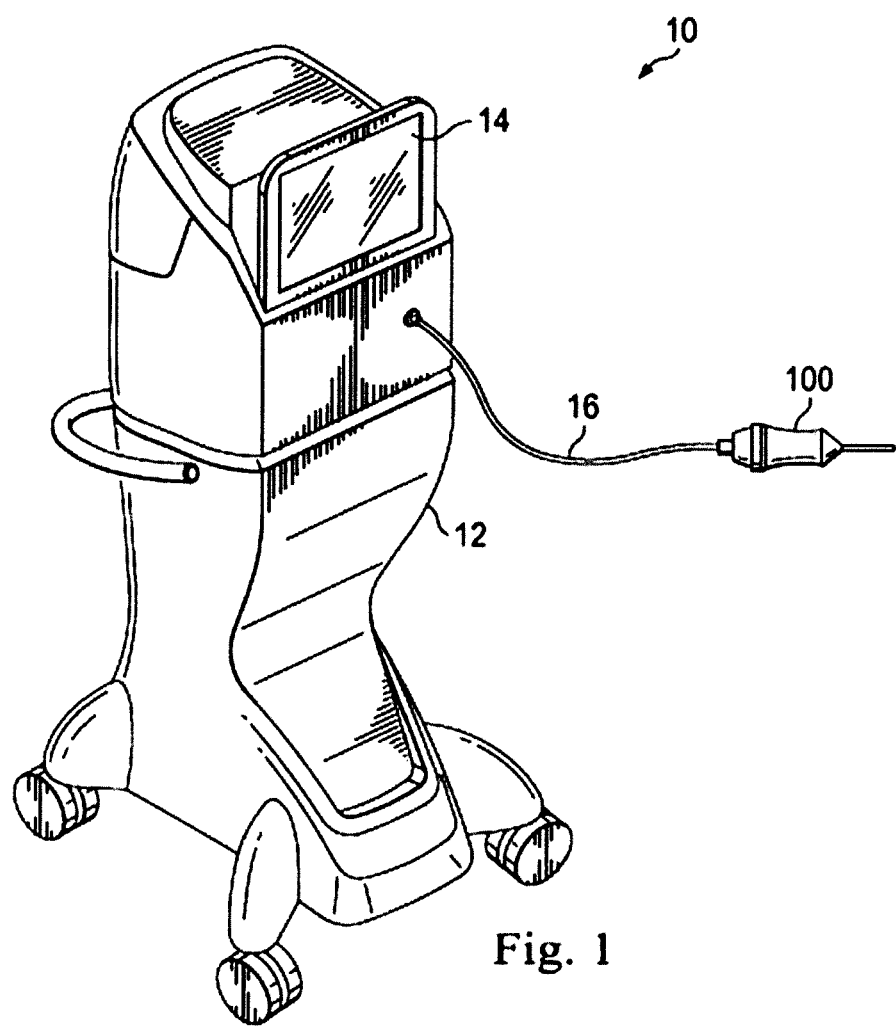
FIG. 1 is an illustration of an exemplary ophthalmic surgical system according to one aspect of the present disclosure implementing the principles and methods described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure is directed to surgical devices, systems, and methods for performing ophthalmic surgeries. The surgical devices include, for example, an ophthalmic probe having reduced pulsing and fluid agitation than prior devices. It does this by minimizing the fluid volume displacement during a cutting cycle. That is, in some embodiments of the present disclosure, the ophthalmic probes include a hollow needle connected with a larger tube by a coupling device that does not oscillate with the hollow needle and with the larger tube. Because of this, the fluid volume within the ophthalmic probe is maintained as relatively constant. This relatively constant fluid volume, therefore, more fully reduces a chance of fluid surge or fluid agitation that may result in undesirable fluid resistance or back flow. This also may result in a smoother, more consistent flow, providing predictability and accuracy for an operating surgeon. In turn, this may result in a better patient outcome.

FIG. 1 illustrates an ophthalmic surgical system, generally designated 10, according to an exemplary embodiment. The surgical system 10 includes a base housing 12 and an associated display screen 14 showing data relating to system operation and performance during an ophthalmic surgical procedure. The surgical system 10 includes an ophthalmic probe 100 structurally configured in a manner that reduces or minimizes fluid surges during the surgical procedure. In some embodiments, the ophthalmic surgical system 10 is a vitrectomy surgical system used to perform vitrectomy procedures to remove vitreous humor or other tissue from the eye.

In some embodiments, the surgical system 10 includes a fluidic pressure source and a probe driver disposed in or forming a part of the base housing 12. In some exemplary embodiments, the fluidic pressure source is a high pressure tank and compressor that provides driving fluidic power to drive the ophthalmic probe 100. Some exemplary pressure sources are pneumatic pressure sources arranged to provide compressed air to drive the ophthalmic probe 100. In some embodiments, the pneumatic pressure source is contained on or in the base housing 12, while in other embodiments, the pressure source is disposed elsewhere in or about the operating room.

The probe driver may be a pressure pulse generator, such as one or more standard three-way or four-way valves, for example. Some embodiments employ a solenoid that displaces a spool between a charge and a discharge position. The probe driver, sometimes referred to as a pressure pulse generator, cycles to set the cutting rate of the ophthalmic probe 100.

The ophthalmic probe 100 and the base housing 12 are in fluid communication with each other along lines 16 representing flow paths or flow lines. Depending on the embodiment, the lines may include a supply line and an aspiration line between the base housing 102 and the ophthalmic probe 100. The supply line may have a lumen that carries a constant or pulsating pressurized fluid for driving an actuator or motor in the ophthalmic probe 100. The aspiration line also extends from the base housing 102 to the ophthalmic probe 100 and is used to aspirate fluid and tissue from the probe 100.

Figure 2:
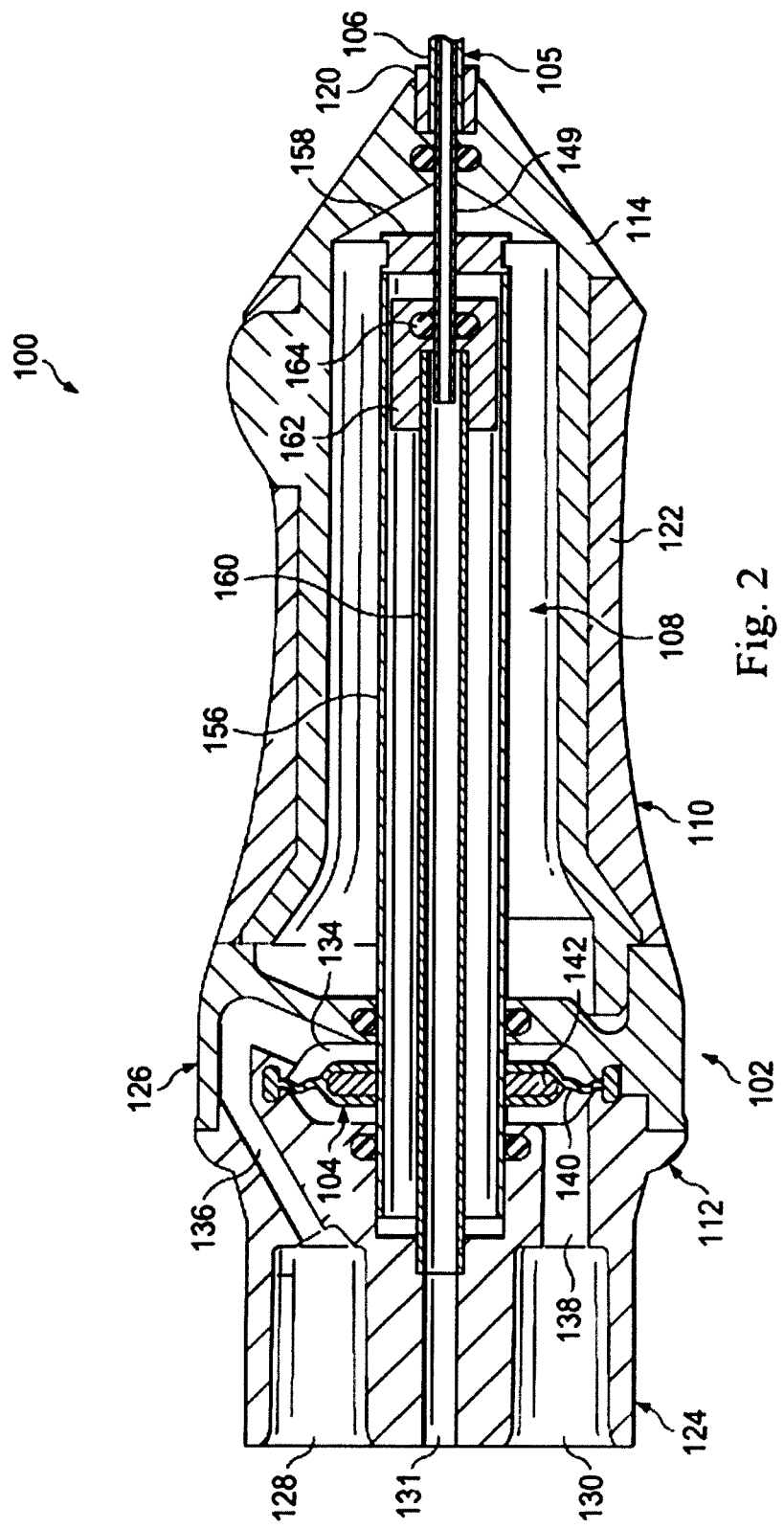
FIG. 2 is a cross-sectional diagram illustrating an ophthalmic probe of the exemplary ophthalmic surgical system of FIG. 1 according to an aspect of the disclosure.

FIG. 2 illustrates a cross-sectional view of an ophthalmic probe 100 according to an exemplary embodiment of the present disclosure for removing fluid/tissue from a patient's eye. In some aspects, the ophthalmic probe 100 is an ophthalmic probe usable in vitrectomy procedures. During such procedures, the probe may be used to penetrate the eye globe to access the vitreous humor or other tissue contained therein. The ophthalmic probe 100 may cut the vitreous humor or other tissue and aspirate it to the base housing 12 of the ophthalmic surgical system 10. It may find particular utility for removing intraocular tissue during an ophthalmic procedure to re-attach a retina of an eye. Although use in an ophthalmic procedure is described, it is to be understood that the ophthalmic probe 100 can be used to cut and aspirate other tissue, such as polyps, fibroids, and other human tissue.

The ophthalmic probe 100 includes a housing 102, a motor 104 disposed within the housing 102, a cutter 105 extending from the housing 102, and a cutter assembly 108.

The housing 102 includes a handle portion 110 and a motor portion 112. The handle portion 110 includes a handle body 114. The handle body 114 extends in a proximal direction from a distal end 120 toward the motor portion 112. An over-molded grip 122 extends about the handle body 114. The grip 122 may be contoured for comfortable grasping by a user.

The motor portion 112 is disposed proximal of the handle portion 110, and includes a rear motor housing 124 and a front motor housing 126. The rear motor housing 124 includes communication ports 128, 130 that provide communication between the ophthalmic probe 100 and the surgical system 10. It also includes an aspiration port 131 that provides communication between an aspiration pump at the surgical system 10 and the probe 100. In this embodiment, the communication ports 128, 130 are pneumatic ports, and the motor portion 112 is configured to hold a fluidically driven motor, such as, for example, a pneumatically driven motor. It's worth noting that other embodiments include alternative probe motors. For example, some embodiments include a fluidically driven piston motor in place of a diaphragm.

The ports 128, 130, 131 extend from the proximal end of the rear motor housing 124 toward the distal end of the rear motor housing 124. The front motor housing 126 is disposed distal of the rear motor housing 124 and is arranged to interface with the handle portion 110. The rear motor housing 124 is configured to provide communication to the surgical system 10, and the front motor housing 126 cooperates with the rear motor housing 124 to securely support the motor 104 of the ophthalmic probe 100.

In this embodiment, the rear motor housing 124 and the front motor housing 126 are shaped to cooperatively form a motor chamber 134. In this embodiment, the chamber 134 is a transversely extending hollow configured to hold the motor 104 for driving the cutter assembly 108. The rear motor housing 124 and front motor housing 126 include passages 136, 138 that respectively extend between the rear motor housing communication ports 128, 130 and the motor chamber 134. In the embodiment of FIG. 2, the ports 128, 130 are in fluid communication with opposing sides of the motor chamber 134, and here, are in communication with the distal and the proximal portions of the motor chamber 134. As such, the ports 128, 130 are in fluid communication with opposing sides of the motor 104.

The motor 104 is disposed within the motor chamber 134 and is configured to drive the cutter assembly 108. In this way, the cutter assembly 108 can be used to cut and aspirate tissue, such as intraocular or other tissue. The motor 104, in this embodiment is a pneumatically driven motor, formed of a flexible diaphragm 140 and a rigid coupler 142. It operates by pressure variation between the first and second ports 128, 130 and thus, on opposing sides of the motor 104. The variation in pressure on opposing sides of the motor 104 within the motor chamber 134 causes the diaphragm 140 to vibrate, carrying portions of the cutter assembly 108 in a back-and-forth oscillating motion.

The distal end of the pneumatic probe 100 includes the cutter 105. The cutter 105 includes a needle 106 and an inner cutting member 149. The needle 106 is a hollow cylinder and extends from the housing 102. It includes a closed end and an outer port that receives tissue, such as ophthalmic tissue, and it cooperates with the cutter assembly 108.

Figure 3:
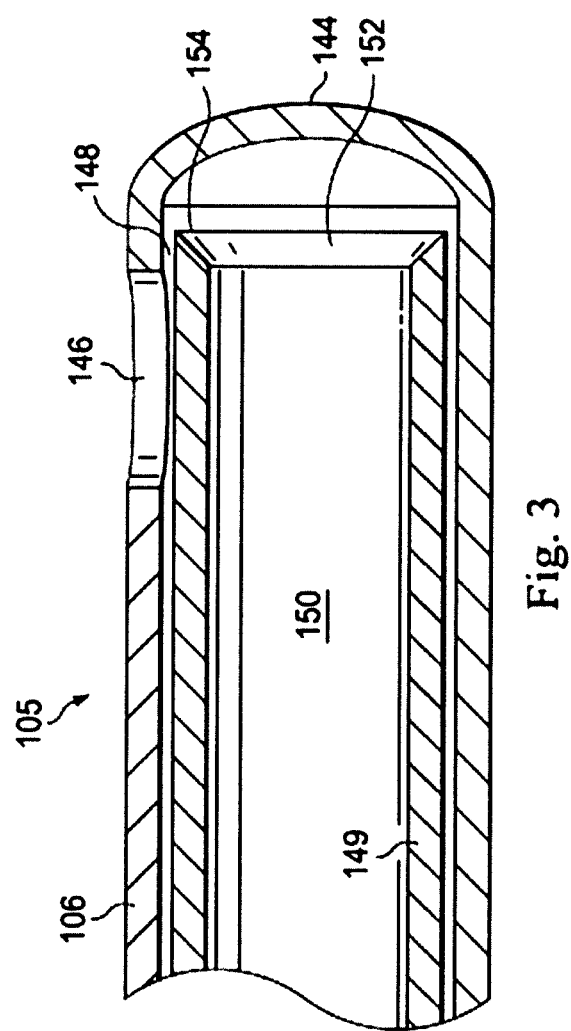
FIG. 3 is a cross-sectional diagram illustrating a distal end of a cutter of the exemplary ophthalmic probe of FIG. 2 according to an aspect of the disclosure.

A distal end of the cutter 105 is shown in FIG. 3. The needle 106 includes a closed end 144 and an outer port 146 that receives tissue, such as ophthalmic tissue. The outer port 146 is in fluid communication with an inner channel 148. The inner cutting member 149 is located within the inner channel 148 of the needle 106. The inner cutting member 149 has an inner bore 150, an open end 152, and a cutting surface 154. As will be described below, the inner bore 150 is in fluid communication with the aspiration line of the ophthalmic probe 100. The aspiration line connects to a vacuum pressure that pulls tissue into the outer port 146 when the inner cutting member 149 is located away from the port 146. The inner cutting member 149 moves within the inner channel 148 of the needle 106 to cut tissue that is pulled into the outer port 146 by the aspiration system. The ophthalmic tissue received by the outer port 146 is preferably vitreous or membranes.

It is worth noting that other embodiments have a distal end of the cutter 105 where a distal end of the inner cutting member 149 includes a port extending radially therethrough. As the edges of the radial port of the inner cutting member 149 pass the edges of the outer port 146 of the outer cutting member, the cutting may take place both on the distal stroke and on the proximal stroke, making a dual cutting cutter. One example of such an embodiment is shown in U.S. Pat. No. 5,106,364, incorporated herein by reference. Other arrangements are also contemplated.

Returning to FIG. 2, the cutter assembly 108 includes a drive shaft 156, a coupler 158, a stationary aspiration tube 160, a cutter seal assembly 162, and the inner cutting member 149. As shown in FIG. 2, the drive shaft 156 connects to and extends from the motor 104 and extends substantially centrally through the body portion 110 toward the distal end of the ophthalmic probe 100. The drive shaft 156 is a relatively larger diameter tube structurally configured to transmit loading applied by the motor 104 to the coupler 158 and ultimately to the inner cutting member 149. In this embodiment, the drive shaft 156 is a cylindrical tube, but other shapes are contemplated. For example, the drive shaft 156 may be a square, a triangle, or other shape having a central passage or opening. As will be described further below, the aspiration tube 160 and the cutter seal assembly 162 are disposed within the lumen or tube of the drive shaft 156. In some embodiments, to reduce mass, the drive shaft 156 is configured of a plurality of longitudinally extending struts or supports, spaced apart by windows or gaps in the drive shaft sidewall. The rigid struts are sufficient to convey oscillating driving force applied by the motor 104 to the distal end of the drive shaft 156. Other arrangements are also contemplated. The drive shaft 156 is configured to carry driving power from the motor to the coupler 158. Accordingly, the drive shaft 156 is a rigidly extending structure.

The coupler 158 is disposed at the distal end of the drive shaft 156 and couples the drive shaft 156 to the cutter inner cutting member 149. In some embodiments, the coupler 158 is disposed within the drive shaft 156. In some examples, it protrudes radially from the exterior surface of the inner cutting member 149 to the inner surface of the drive shaft 156. Like the drive shaft 156, the coupler 158 is a rigid structure configured to convey the oscillating displacement from the drive shaft 156 to the inner cutting member 149. It may be solid or may be formed with windows or gaps to decrease its overall weight and decrease its dampening effect on the oscillating motor 104. In this embodiment, the drive shaft 156, the coupler 158, and the inner cutting member 149 are all coaxially aligned in the ophthalmic probe 100.

As the drive shaft 156 axially translates in a distal and proximal direction, the coupler 158, fixed to the drive shaft 156, also translates in an oscillating manner. Because the inner cutting member 149 is fixed to the coupler 158, axial displacement or translation of the coupler 158 results in axial displacement or translation of the inner cutting member 149 relative to the needle 106.

The stationary aspiration tube 160 and the cutter seal assembly 162 are disposed within the drive shaft 156. These form a portion of an aspiration pathway through the ophthalmic probe 100. For example, the aspiration pathway includes the port 146, the inner cutting member 149, the aspiration tube 160, and the aspiration port 131. In the exemplary embodiment shown, the aspiration tube 160 and the cutter seal assembly 162 are fixed in place relative to the body portion 110 of the ophthalmic probe 100. As such, as the drive shaft 156, the coupler 158, and the inner cutting member 149 oscillate via the motor 104, the aspiration tube 160 and the cutter seal assembly 162 are substantially fixed in place.

In the embodiment shown, the aspiration tube 160 is a tube affixed coaxially with the inner cutting member 149 and extends from the inner cutting member 149 to a position proximal of the motor 104. Accordingly, in the exemplary embodiment in FIG. 2, it is also coaxial with the drive shaft 156. The aspiration tube 160 has a diameter greater than the diameter of the inner cutting member 149 so that the aspirating flow can be more easily induced without the same levels of pressure loss encountered in the smaller diameter inner cutting member 149. Here, the aspiration tube 160 is coaxially aligned with the aspiration port 131, and the aspiration tube 160 may be connected directly to the aspiration line of the lines 16 (FIG. 1) connecting the ophthalmic probe to the base housing 12 of the ophthalmic surgical system 10.

The cutter seal assembly 162 connects the distal portion of the aspiration tube 160 to the inner cutting member 149. In this embodiment, the cutter seal assembly 162 is fixed relative to the aspiration tube 60 and, therefore, the inner cutting member 149 moves relative to the cutter seal assembly 162. The cutter seal assembly also transitions the aspiration pathway from the smaller diameter inner cutting member 149 to the larger diameter aspiration tube 160. The cutter seal assembly 162 is attached at the distal end of the aspiration tube 160 and is configured to house one or more seals 164 that seal around the inner cutting member 149 to prevent leakage of aspiration fluid from the aspiration pathway and prevent drawing of air into the aspiration pathway from the inner portions of the body portion 110. In the embodiment shown, the seal 164 is an O-ring, although other seals may be used. In this embodiment, the cutter seal assembly 162 is sized to receive the distal end of the aspiration tube 160 therein, and may be glued, laser or spot welded, or otherwise adhered to the aspiration tube 160.

Since the cutter seal assembly 162 is fixed in place relative to the aspiration tube 160, and the aspiration tube 160 is substantially or completely fixed in place relative to the body portion of the ophthalmic probe 100, the volume change within the aspiration tube 160 as a result of the oscillating inner cutting member 149 is minimized, resulting in a decreased chance of fluid surge within the aspiration line compared to vitrectomy probes that have a coupler that moves with inner cutting member 149. This becomes apparent with reference to FIG. 4.

Figure 4:
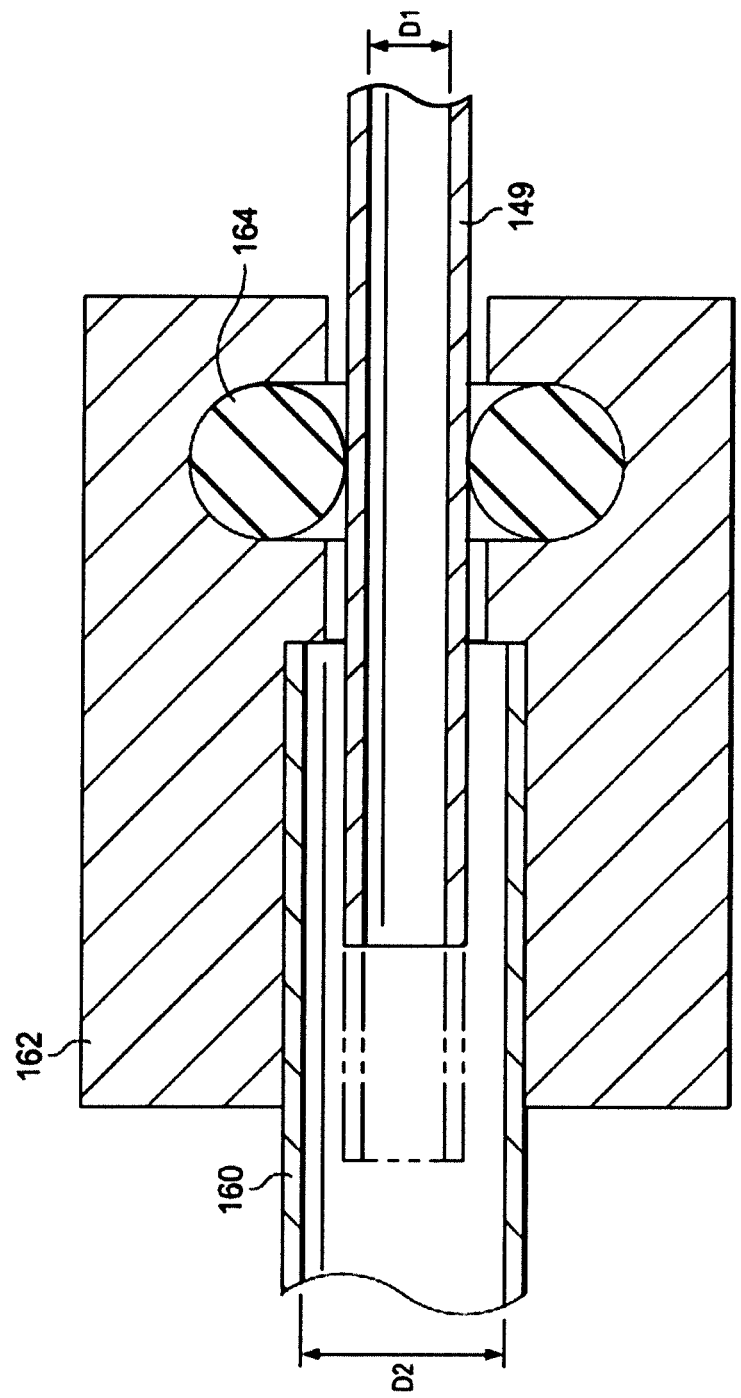
FIG. 4 is a detailed view of a portion of the ophthalmic probe of FIG. 2 according to an aspect of the disclosure.

FIG. 4 shows an enlarged view of the cutter seal assembly 162 and a portion of the aspiration tube 160 and the inner cutter member 149. As can be seen the inner cutting member 149 has a first smaller diameter D1 and the aspiration tube 160 has a second larger diameter D2. In order to reduce pressure loss occurring from long lengths of fluid pathways with minimal diameters, the aspiration pathway is designed to expand to promote more consistent and easier flow. Accordingly, the aspiration flow is configured to expand from the minimal diameter of the inner cutting member 149 to the larger diameter of the aspiration tube 160.

In this example, the inner cutting member 149 is disposed at the extreme distal position during a cutting cycle. The dashed lines indicate the position of the inner cutting member 149 at an extreme proximal position during a cutting cycle. The dashed lines also represent the change in volume that occurs locally within the aspiration pathway as a result of the displaced inner cutting member 149 during a cutting cycle. As can be seen in FIG. 4, the change in volume that occurs within the aspiration pathway is limited to the volume displaced by the inner cutting member 149. Because the inner cutting member has a small outer diameter (in the range of about 0.025 to 0.012 in.) and an inner diameter (in the range of about 0.020 to 0.010 in.), and because the cutting cycle axial displacement is often in the range of about 0.010-0.050 in., the total volume displacement is minimal. In some embodiments, the total volume displacement is less than about $9 \times 10^{-6}$ in$^3$, and in other embodiments, the total volume displacement is less than about $4 \times 10^{-7}$ in$^3$. Yet other values and ranges are contemplated.

The displacement volume in the aspiration pathway of the ophthalmic probe 100 may be a substantially smaller displacement volume than can be achieved in conventional devices where a coupler is disposed in place of the cutter seal assembly. The conventional coupler fixedly connects to the inner cutting member and therefore moves with the inner cutting member. As both the coupler and the inner cutting member oscillate during a cutting cycle in the conventional device, the fluid volume displacement is much larger than when only the inner cutting member oscillates. The fluid volume displacement in conventional devices may be as much as, for example only, 7-50 times larger (depending on the size of the inner cutting member) than the volume displacement that occurs in the system disclosed herein. This large displacement in prior devices may manifest itself as pulses or fluid surges. In some instances, this may result in a reversal of flow during vitrectomy cutting or in agitation resulting in gas coming out of solution.

In use, a surgeon sets a cutting rate at the surgical base housing 112. The fluidic pressure source and the probe driver drive the motor 104 to actuate the cutter assembly 108 at the designated cutting rate. It does this by driving the drive shaft 156 at the designated cutting rate. The drive shaft 156 is rigidly fixed to and drives the coupler 158. The coupler 158 is rigidly fixed to and drives the inner cutting member 149. Since the drive shaft 156 and the coupler 158 operate within air, and do not physically contact or disrupt fluid or tissue, the dampening effect is smaller than if the drive shaft 156 and the coupler 158 were to be in contact with the aspiration fluid or if maintained within a fluid chamber.

Accordingly, during a cutting cycle, when the motor drives the drive shaft and the coupler in the distal direction, the inner cutting member 149 makes a cutting motion in the needle 106 by advancing across the port 146 until it is closed. As this occurs, the proximal end of the inner cutting member 149 moves distally relative to the aspiration tube 160 and the cutter seal assembly 162. Because only the inner cutting member 149 moves distally, there is very little volume change in the aspiration pathway, and the aspiration flow is only minimally affected.

When the inner cutting member 149 reaches the distalmost position, the motor drives the cutter assembly 108 in the proximal direction. Again, it does this by moving the drive shaft 156, the coupler 158, and the inner cutting member 149 in the distal direction. This opens the port 149 permitting additional fluid and tissue to enter the needle 106. As the inner cutting member 149 moves in the proximal direction, its volume within the aspiration tube 160 increases as shown in FIG. 4. Since the aspiration tube 160 and the cutter seal assembly 162 are fixed in place, only the inner cutting member 149 affects the volume within the aspiration pathway. Because only the inner cutting member 149 moves proximally, there is very little volume change in the aspiration pathway, and the aspiration flow is only minimally affected.

Figure 5:
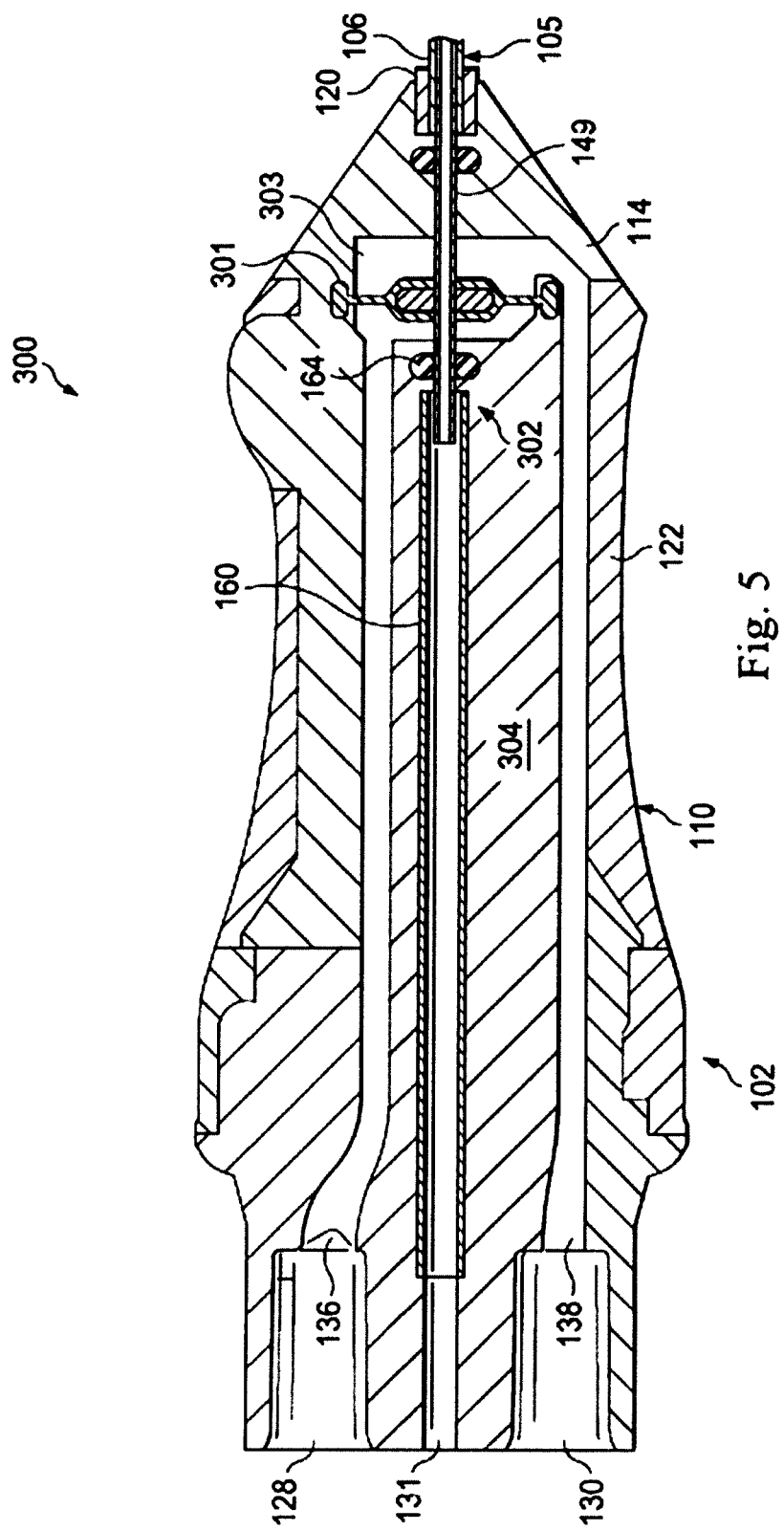
FIG. 5 is a cross-sectional diagram illustrating another ophthalmic probe of the exemplary ophthalmic surgical system of FIG. 1 according to an aspect of the disclosure.

FIG. 5 illustrates another cross-sectional view of an ophthalmic probe 300 (which in some embodiments is the probe 100). The probe 300 includes many features similar to the probe 100 discussed herein. For the sake of simplicity, some reference numbers are used to designate the same or similar parts. For example, the ophthalmic probe 300 includes a housing 102 and a cutter 105 extending from the housing 102. The probe 300 also includes a motor 301 disposed within a motor chamber 303 in the housing 102, and includes a cutter assembly 302. In this embodiment, the cutter assembly 302 includes the stationary aspiration tube 160, a cutter seal housing portion 304, and the inner cutting member 149. The cutter seal housing portion 304 is fixed in place and does not move relative to the stationary aspiration tube 160 and therefore, does not move relative to the probe housing 102. While the stationary aspiration tube 160 is shown in the cross-sectional view of FIG. 5 as a separate component from the body 102, other embodiments have the stationary aspiration tube 160 formed as a part of the body with the stationary aspiration tube 160 being an integral or monolithic portion of the body 102.

In this embodiment, the motor 301 is connected directly to the inner cutting member 149 in a manner that drives the inner cutting member 149 in a cutting cycle. Accordingly, only the inner cutting member 149 moves within the aspiration pathway, and therefore, similar to the embodiment in FIG. 2, there is very little volume change in the aspiration pathway during a cutting cycle. In this example, the motor 301 is disposed in the distal portion of the probe 300. Also in this example, the motor 301 is disposed distal of the proximal end of the inner cutting member 149 and is configured to drive the inner cutting member 149.

The motor 301 may be similar to the motor 104 and may include a flexible diaphragm and a rigid coupler that operates by pressure variation between the first and second ports 128, 130. The variation in pressure on opposing sides of the motor 301 within the motor chamber causes the diaphragm 140 to vibrate, carrying the inner cutting member 149 in a back-and-forth oscillating motion. Other arrangements are also contemplated.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmic apparatus for performing an ocular surgery, comprising:
    an ophthalmic probe body with a handle portion graspable by a user;
    an aspiration port on a proximal portion of the probe body;
    an aspiration tube, coupled to the aspiration port, disposed within the probe body and having a lumen arranged to contact aspiration fluid flowing therethrough;
    a cutter extending from a distal portion of the probe body and comprising a first cutting member and a second cutting member, the first cutting member being at least partially disposed within and moveable relative to the second cutting member, the first cutting member having a lumen having a first diameter, the second cutting member having a distal end with a port formed therein for receiving patient tissue, the first cutting member configured to be axially displaceable within the second cutting member to sever the patient tissue received in the second cutting member port, wherein the first cutting member also moves within a portion of the lumen of the aspiration tube; and
    a motor within the distal portion of the probe body, on an opposite side of the probe body as the aspiration port, wherein the motor is connected directly to the first cutting member to actuate the first cutting member relative to the second cutting member and the lumen of the aspiration tube;
    a pneumatic port adjacent the aspiration port on the proximal portion of the probe body; and
    a pneumatic channel, inside the probe body, coupled to the pneumatic port and configured to deliver air to at least one side of the motor;

wherein the pneumatic channel runs along a majority of a length of the probe body.

2. The ophthalmic apparatus of claim 1, wherein the motor is disposed between the aspiration tube and the second cutting member.

3. The ophthalmic apparatus of claim 1, wherein the lumen of the aspiration tube has a diameter larger than an outer diameter of the first cutting member.

4. The ophthalmic apparatus of claim 1, wherein the second cutting member and the aspiration tube are statically connected to the probe body.

5. The ophthalmic apparatus of claim 1, wherein the first cutting member, the second cutting member, and the aspiration tube form an aspiration pathway configured to aspirate the tissue cut during the ocular surgery.

6. The ophthalmic apparatus of claim 1, wherein the first cutting member is coaxial with the second cutting member and the lumen of the aspiration tube.

7. The ophthalmic apparatus of claim 1, further comprising a cutter seal affixed to the second cutting member, the cutter seal configured to prevent fluid from passing between the first cutting member and the second cutting member.

8. An ophthalmic apparatus for performing an ocular surgery, comprising:
an ophthalmic probe body with a handle portion graspable by a user;
an aspiration port on a proximal portion of the probe body;
a first stationary aspiration tube, coupled to the aspiration port, having a first aspiration lumen disposed within the probe body, the first aspiration lumen arranged to contact aspiration fluid flowing therethrough;
a cutting assembly comprising an axially displaceable cutting member forming a second aspiration lumen, the cutting member movably disposed within a portion of the first aspiration lumen, the first and second aspiration lumens configured to aspirate fluid through the probe body; and
a motor within a distal portion of the probe body, on an opposite side of the probe body as the aspiration port, configured to actuate the cutting member relative to the first aspiration lumen;
a pneumatic port adjacent the aspiration port on the proximal portion of the probe body; and
a pneumatic channel, inside the probe body, coupled to the pneumatic port and configured to deliver air to at least one side of the motor;
wherein the pneumatic channel runs along a majority of a length of the probe body.

9. The ophthalmic apparatus of claim 8, wherein the first stationary aspiration tube and the cutting assembly form an aspiration pathway configured to aspirate tissue cut during the ocular surgery.

10. The ophthalmic apparatus of claim 8, wherein the lumen of the aspiration tube has a diameter larger than an outer diameter of the axially displaceable cutting member.

11. The ophthalmic apparatus of claim 8, wherein the motor is disposed between the first stationary aspiration tube and an outer cutting member of the cutting assembly, wherein the motor is configured to actuate the axially displaceable cutting member inside the outer cutting member.

12. The ophthalmic apparatus of claim 11, wherein the first aspiration lumen and the outer cutting member are statically connected to the probe body.

13. The ophthalmic apparatus of claim 11, wherein the axially displaceable cutting member is coaxial with the first aspiration lumen and the second aspiration lumen.

14. The ophthalmic apparatus of claim 11, further comprising a cutter seal affixed to the axially displaceable cutting member.

* * * * *